US011077222B2

(12) United States Patent
Zaludova et al.

(10) Patent No.: US 11,077,222 B2
(45) Date of Patent: *Aug. 3, 2021

(54) SCENT GLASS

(71) Applicant: Hya-Scent, Inc., San Francisco, CA (US)

(72) Inventors: Helena Zaludova, San Francisco, CA (US); Martin Schnitzer, Graz (AT)

(73) Assignee: Hya-Scent, Inc., San Francisco, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/405,947

(22) Filed: May 7, 2019

(65) Prior Publication Data
US 2019/0262492 A1 Aug. 29, 2019

Related U.S. Application Data

(63) Continuation of application No. 15/782,794, filed on Oct. 12, 2017, now Pat. No. 10,279,067.

(60) Provisional application No. 62/407,410, filed on Oct. 12, 2016.

(51) Int. Cl.
*A61L 9/12* (2006.01)
(52) U.S. Cl.
CPC .................. *A61L 9/127* (2013.01)
(58) Field of Classification Search
CPC ... A61L 9/04; A61L 9/12; A61L 9/127; A61L 2209/134
See application file for complete search history.

(56) References Cited

U.S. PATENT DOCUMENTS

| | | | |
|---|---|---|---|
| 940,604 | A | 11/1909 | Leathers |
| 1,994,932 | A | 3/1935 | Lucien |
| 2,120,204 | A | 6/1938 | Langhorst |
| 2,597,195 | A | 5/1952 | Smith |
| 2,802,695 | A | 8/1957 | Johnson |
| 2,804,291 | A | 8/1957 | Segerstad |
| 2,847,976 | A | 8/1958 | Spaulding |
| 3,283,787 | A | 11/1966 | Davis |
| 3,550,853 | A | 12/1970 | Gray |

(Continued)

FOREIGN PATENT DOCUMENTS

DE 102010026849 A1 * 1/2012 ............. A61L 9/127
EP 0864330 9/1998
(Continued)

OTHER PUBLICATIONS

Diptyque Hourglass Diffuser Product Reference, Mar. 15, 2014, 6 pages.
(Continued)

*Primary Examiner* — Darren W Gorman
(74) *Attorney, Agent, or Firm* — Aka Chan LLP

(57) ABSTRACT

A fragrance diffuser has a diffuser element connecting a first reservoir to a second reservoir. As a fragrant oil flows between the reservoirs, the diffuser element becomes saturated with oil and diffuses the fragrance or scent. The diffuser is self-contained, easy to interact with, without creating a mess. The diffuser is relaxing and pleasant to watch as it flows through from one end and drips to the other, releasing one small bubble at a time. It is refillable, transportable, and the intensity of the scent release can be controlled easily by saturating the wood more or less often.

19 Claims, 14 Drawing Sheets

(56) References Cited

U.S. PATENT DOCUMENTS

| | | | |
|---|---|---|---|
| 3,685,734 | A | 8/1972 | Paciorek et al. |
| 3,972,473 | A | 8/1976 | Harrison |
| 4,084,732 | A | 4/1978 | Dearling |
| 4,145,001 | A | 3/1979 | Weyenberg et al. |
| 4,149,675 | A | 4/1979 | Van Breen et al. |
| 4,158,440 | A | 6/1979 | Sullivan et al. |
| 4,226,829 | A | 10/1980 | Mike |
| 4,286,754 | A | 9/1981 | Jones |
| 4,413,779 | A | 11/1983 | Santini |
| 4,454,987 | A | 6/1984 | Mitchell |
| 4,605,165 | A | 8/1986 | Van Loveren et al. |
| 4,726,519 | A | 2/1988 | Muoio |
| 4,747,539 | A | 5/1988 | Spector |
| 4,780,253 | A | 10/1988 | Fukuhara et al. |
| 5,050,798 | A | 9/1991 | Sullivan |
| 5,069,231 | A | 12/1991 | Rutherford |
| 5,139,864 | A | 8/1992 | Lindauer |
| 5,242,111 | A | 9/1993 | Nakoneczny et al. |
| 5,263,274 | A | 11/1993 | Speed |
| 5,361,522 | A | 11/1994 | Green |
| 5,364,027 | A | 11/1994 | Kuhn |
| 5,556,030 | A | 9/1996 | Paul |
| 5,755,381 | A | 5/1998 | Yazaki |
| 5,845,847 | A | 12/1998 | Martin et al. |
| 6,050,551 | A | 4/2000 | Anderson |
| 6,481,639 | B1 | 11/2002 | Pozzo |
| 6,551,560 | B1 | 4/2003 | Flashinski et al. |
| 6,899,280 | B2 | 5/2005 | Kotary et al. |
| 6,913,733 | B2 | 7/2005 | Hardy et al. |
| 6,994,799 | B2 | 2/2006 | Van Driessche et al. |
| 7,481,380 | B2 | 1/2009 | Kvietok et al. |
| 2006/0076429 | A1 | 4/2006 | Kvietok et al. |
| 2006/0097065 | A1 | 5/2006 | Kvietok et al. |
| 2006/0233538 | A1 | 10/2006 | Tollens et al. |
| 2007/0023541 | A1 | 2/2007 | Brown et al. |
| 2007/0176015 | A1 | 8/2007 | Farrell et al. |
| 2015/0190542 | A1 | 7/2015 | Lamboux et al. |

FOREIGN PATENT DOCUMENTS

| | | |
|---|---|---|
| EP | 1088562 | 4/2001 |
| EP | 1076014 | 12/2004 |
| FR | 3019048 | 10/2015 |
| WO | 2005032606 | 4/2005 |
| WO | 2011128604 | 10/2011 |

OTHER PUBLICATIONS

International Search Report, PCT Application PCT/US2017/056416, dated Mar. 1, 2018, 3 Pages.
Diptyqueparis, Le sablier de diptyque par R'Pure Studio / diptyque's hourglass by R'Pure Studio, Sep. 10, 2012, URL: https://www.youtube.com/watch?v=Bg2-h4Q6hvk.
European Patent Office, Extended European Search Report, EP Application No. 17859437.0, dated May 4, 2020, 9 pages.

* cited by examiner

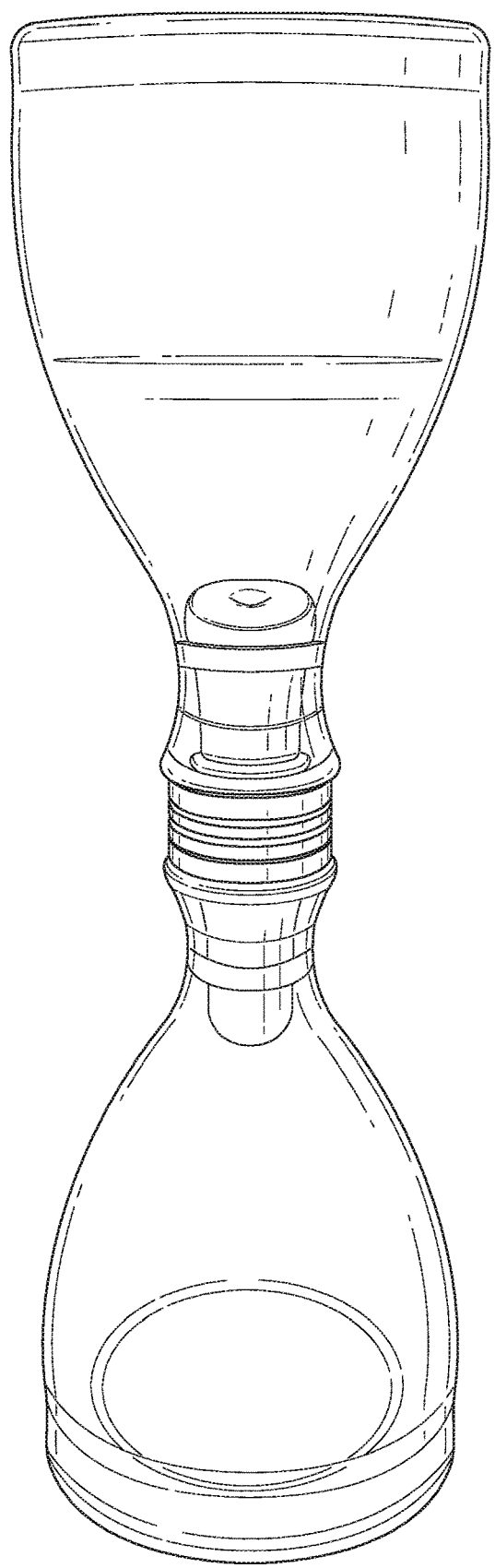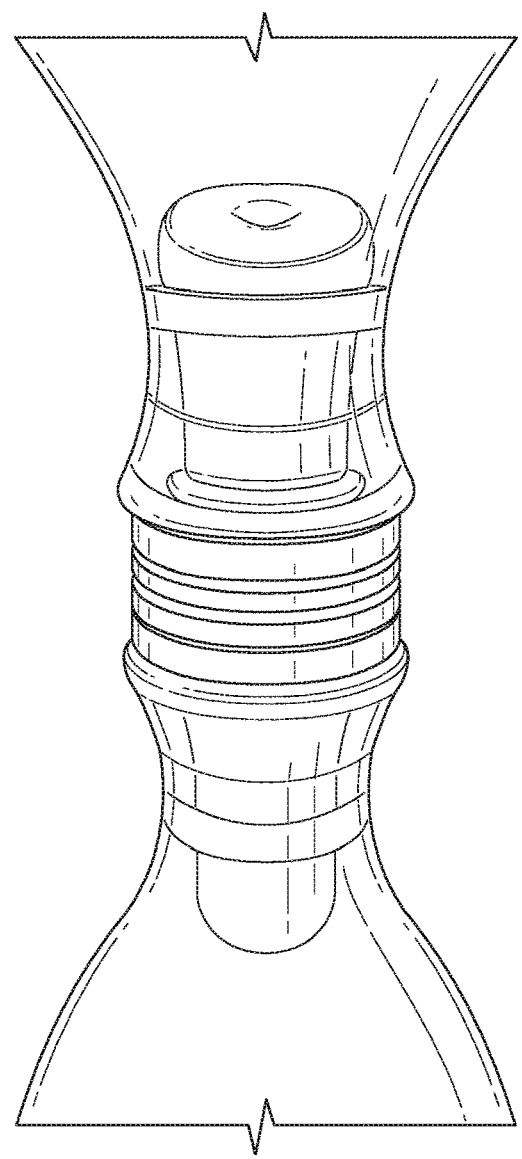
FIG. 1
FIG. 2

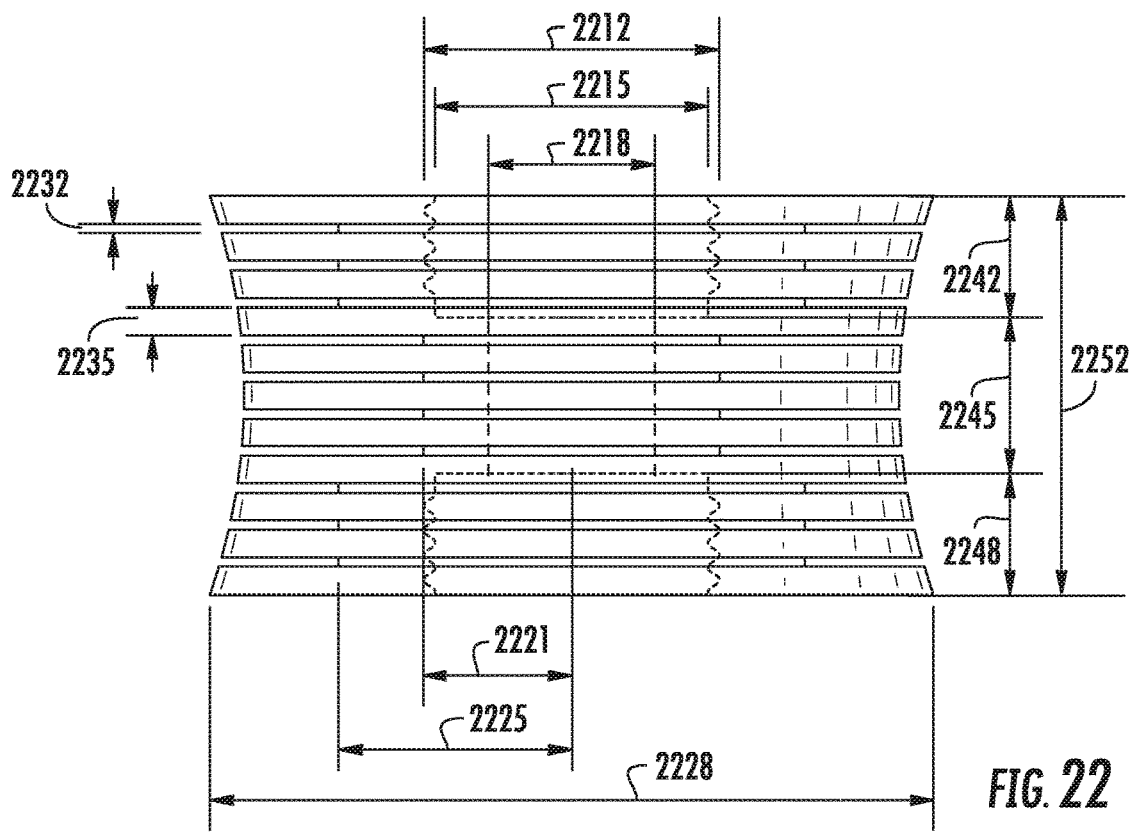
FIG. 22
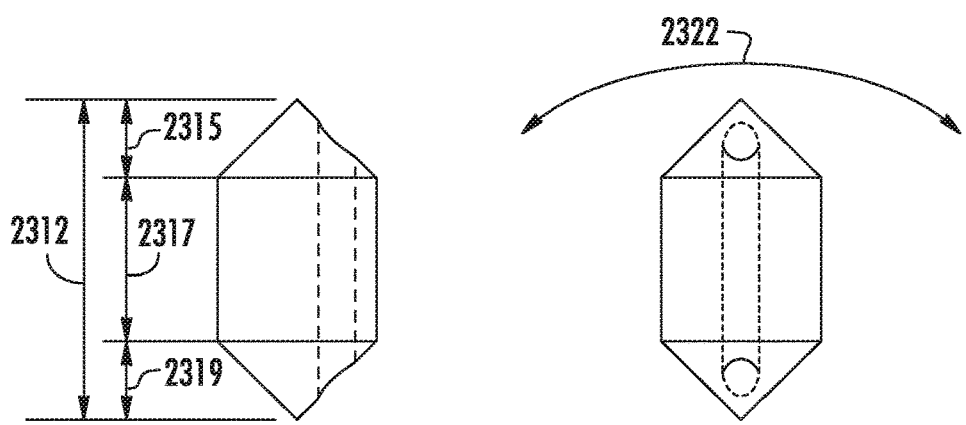
FIG. 23A
FIG. 23B
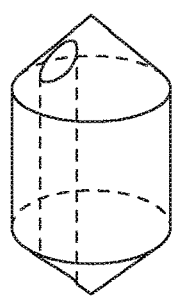
FIG. 23C
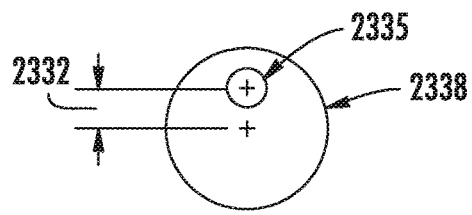
FIG. 23D

SCENT GLASS

CROSS-REFERENCE TO RELATED APPLICATIONS

This patent application is a continuation of U.S. patent application Ser. No. 15/782,794, filed Oct. 12, 2017, issued as U.S. Pat. No. 10,279,067 on May 7, 2019, which claims the benefit of U.S. patent application 62/407,410, filed Oct. 12, 2016. These applications are incorporated by reference along with all other references cited in this application.

BACKGROUND OF THE INVENTION

The invention generally relates to devices or apparatuses to dispense fragrances, and more specifically to a fragrance or scent diffuser.

Human beings have fives senses, smell being one of the most important. Smell influences health, memory, emotions, and many other aspects of a person's life and well being. People like the places and environment they are in to smell good. Ultimately, a person surrounded by good smells has a better and happier life. Indeed, the global fragrance market is substantial and continues to grow.

People want better ways to spread good smells. Some ways to dispense fragrances include: reed diffusers, candles, plug-in diffusers, gel diffusers, room sprays, potpourri, and ultrasonic mist devices. Despite the success of such products for use as air fresheners and in aromatherapy, there are shortcomings.

Some disadvantages of these products are: Reed diffusers: spill prone, release is not timed, cannot be transported easily once opened, damages furniture when spilled, and messy to touch. Candles: open fire is not allowed in many public spaces, smoke after blowing it out, not refillable, and conspicuous when used during daylight hours. Plug-in diffusers: not natural and not decorative. Gel diffusers: not natural oil, not interactive, not elegant, and not refillable. Room sprays: evaporates quickly, and not natural. Potpourri: no time release, not interactive, not elegant, and not refillable. Ultrasonic mist devices: needs to be plugged in, and not interactive.

Therefore, there is a need for an improved device, apparatus, and technique for dispensing fragrances and scents.

BRIEF SUMMARY OF THE INVENTION

A fragrance diffuser has a diffuser element connecting a first reservoir to a second reservoir. As a fragrant oil flows between the reservoirs, the diffuser element becomes saturated with oil and diffuses the fragrance or scent. The diffuser is self-contained, easy to interact with, without creating a mess. The diffuser is relaxing and pleasant to watch as it flows through from one end and drips to the other, releasing one small bubble at a time. It is refillable, transportable, and the intensity of the scent release can be controlled easily by saturating the wood more or less often.

In an implementation, two glass containers are connected by a wood piece that absorbs scented liquid which passes through it, soaks it up, and as it evaporates it diffuses scent into its environment. The wood piece has a hole which goes all the way through it and two to three others that allow the liquid to fully penetrate and saturate the wood. The wood piece has two layers: the inner which is solid and fully saturates, and outer that is cut into slats or ridges. The outer layer remains dry or relatively dry to the touch and the spaces in between allow for the evaporation, leading to scent diffusion of the inner layer.

The wooden piece has two narrower ends which are cut at a precise angle that allows the liquid to drip through between the two glass containers. The wood piece also has two plastic O-rings that function as a barrier to prevent the scented liquid from seeping through outside of the small holes in the wood. In other implementations, the wood pieces are bonded to prevent excess leaking of the liquid. The glass containers are identical in shape and size and can be made of other nonpermeable materials.

In an implementation, an apparatus includes: a first reservoir having a first opening to a first chamber of the first reservoir; a second reservoir having a second opening a second chamber of the first reservoir; a diffuser element, where the diffuser element includes cellulose (e.g., wood), the diffuser element is connected between the first opening of the first reservoir and the second opening of the second reservoir, and an outer surface of the diffuser element includes slats and grooves, and the slats extend parallel to each other; and a first channel, extending through the diffuser element, the first channel connecting the first chamber to the second chamber.

In an implementation, an apparatus includes: a first reservoir having a first opening to a first chamber of the first reservoir, where the first opening includes a first male threaded portion; a second reservoir having a second opening a second chamber of the first reservoir, where the second opening includes a second male threaded portion; a diffuser element, where the diffuser element includes cellulose (e.g., wood), the diffuser element is connected between the first opening of the first reservoir and the second opening of the second reservoir, and an outer surface of the diffuser element includes slats and grooves, and the slats extend parallel to each other; a first threaded female receptacle, formed in a first end of the diffuser element, where the first threaded female receptacle connects to or mates with the first male threaded portion of the first reservoir; a second threaded female receptacle, formed in a second end of the diffuser element, opposite to the first end, where the second threaded female receptacle connects to or mates with the second male threaded portion of the second reservoir; a first gasket, connected between the first threaded female receptacle of the diffuser element and the first opening of the first reservoir; a second gasket, connected between the second threaded female receptacle of the diffuser element and the second opening of the first reservoir; and a first channel, extending through the diffuser element, the first channel connecting the first chamber to the second chamber.

In an implementation, a method includes: providing a first reservoir having a first opening to a first chamber of the first reservoir; providing a second reservoir having a second opening a second chamber of the first reservoir; connecting a diffuser element between the first and second reservoirs, where the diffuser element includes cellulose, the diffuser element is connected between the first opening of the first reservoir and the second opening of the second reservoir, and an outer surface of the diffuser element includes slats and grooves, and the slats extend parallel to each other; and providing a first channel, extending through the diffuser element, the first channel connecting the first chamber to the second chamber.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 1 shows an implementation of a scent glass diffuser.

FIG. 2 shows enlarged view of a diffuser element of the diffuser.

FIGS. 21-22 show details of a diffuser ring element of a fragrance diffuser.

FIGS. 23A-23D show details of a wood core element of a fragrance diffuser.

DETAILED DESCRIPTION OF THE INVENTION

FIG. 1 shows an implementation of a scent glass diffuser including glass containers, diffuser element, O-rings, and fragrant oil. FIG. 2 shows enlarged or close-up view of the diffuser element.

Figure 3:
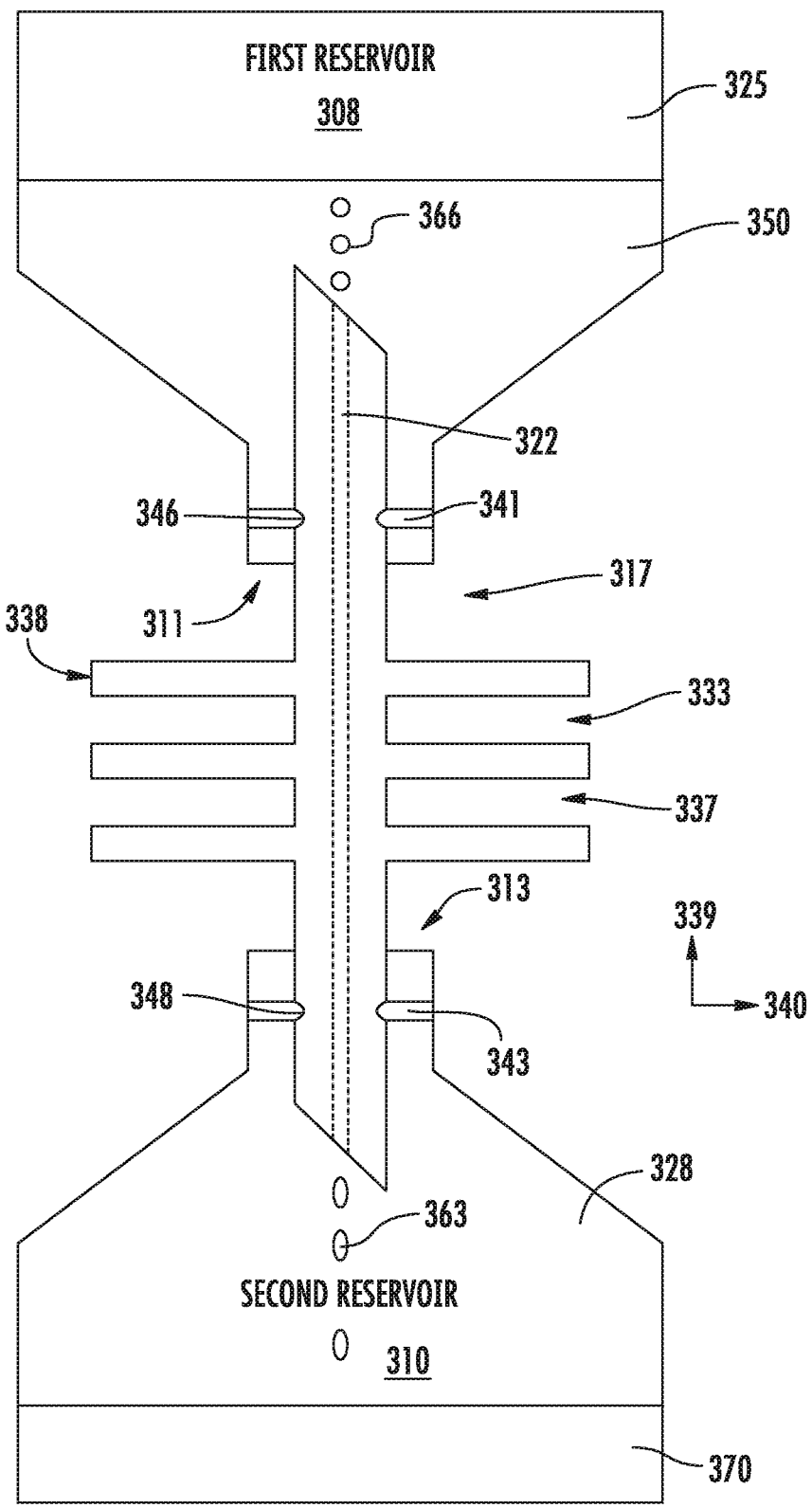
FIG. 3 shows a functional block diagram of a diffuser.

FIG. 3 shows a functional block diagram of a fragrance diffuser or diffuser. An implementation of the fragrance diffuser is referred to as "scent glass." The diffuser includes a first reservoir 308 and a second reservoir 310. The first reservoir has an opening 311, and the second reservoir has an opening 313.

The reservoirs can be glass containers, flasks, or jars, but can be vessels of any material that can hold a liquid, including polymers, plastics, polycarbonate, and the like. The reservoirs are transparent or translucent (e.g., frosted or etched material) so the contents of the reservoir are visible from an exterior of the reservoir. The user will be able to check a level of the oil in the diffuser. However, in other implementations, the reservoir can be opaque. Both reservoirs can have the same shape, or can be different shapes. The glass can be blown glass, crystal, or leaded crystal.

There is a diffuser or diffusing element 317. The diffuser element is connected between opening 311 of the first reservoir and opening 313 of the second reservoir. The diffuser element has an internal channel 322 (shown in broken lines) extending through it. The channel connects an interior chamber 325 of the first reservoir to an interior chamber 328 of the second reservoir. In an implementation, the diffuser element is made from a wood, plant-based, or cellulose fiber materials. However, in other implementation, other materials may be used that provide an equivalent diffusing capability or functionality.

An outer surface of the diffuser element includes a number of grooves 333 and 337. The grooves extend parallel to each other. The diffuser element can have any number of grooves, more or fewer than shown in the figure, such as 2, 3, 4, 5, 10, 20, or more grooves. The grooves extend around the diffuser element. A slat or ridge 338 is formed by the grooves, such as one slat between two grooves. The slat or ridge may also be referred to as a fin or protrusion. The grooves may be considered spaces adjacent to the slats or ridges.

As shown in FIGS. 1-2, in three dimensions, the groove forms a cylindrical shape, and the slats or ridges form what appear as parallel disks. The shape of the disks can be a circle, but other shapes in other implementations such as ellipse, oval, obround, polygonal, square, rectangular, or other. The grooves and slats or ridges are symmetric about an axis through a middle or center of the diffuser element in a first direction 339, while slats or ridges extend transverse or perpendicular to the axis in a second direction 340. The slats or ridges are oriented perpendicular to the direction of the flow of oil through the channel. However, in other implementations, the slats or ridges can be oriented parallel to first direction 339 or other angles relative to the axis or oil flow direction.

In an implementation, an overall length of the diffuser element in first direction 339 is greater than an overall width in second direction 340. However, in other implementations, the length of the diffuser element in first direction 339 is less than the width in second direction 340.

There are O-rings, gaskets, washers, or seals 341 and 343 connected to indentations 346 and 348 of the diffuser element. Gasket 341 seals the opening 311 of the first reservoir, which prevents a fragrant oil 350 from leaking out of the reservoir. Gasket 343 seals the opening 313 of the second reservoir. The gasket can be rubber, neoprene, or other material that is compatible with and can seal oil or other liquids. Although only a single gasket is described per side, there can be multiple gaskets, such as 2, 3, 4, or more gaskets per side, as needed to improve the seal. Typically, there are the same number of gaskets per side, but the number can be different (in any combination such as 1 and 2, and 2 and 3).

In other embodiments, there are threads notched into the wood that allow for the glass reservoir to be attached and detached by screwing it in. There are round gaskets at the bottom of the threading that seal the top of the glass reservoir neck to the wood. The glass reservoir can also be attached by a partial puzzle snap fit of the neck to the wood with a precise lock-in-groove mechanism.

A package or kit includes a scent glass or fragrance diffuser with an aromatic fragrance oil or liquid prefilled in one of the reservoirs (e.g., a first reservoir). To use, a user places diffuser on a table or other surface in a space or place where the user wants to dispense the fragrance. Each reservoir has a relatively flat base surface which can rest stably on a flat surface.

So the fragrance oil can saturate the diffuser element, the diffuser is placed on the surface such that a reservoir (e.g., first reservoir) with oil (e.g., oil 350) is above the diffuser element and the other reservoir (e.g., second reservoir). The oil will flow, via gravity, into contact with the diffuser element, which absorbs some of the oil. And some of the oil will pass through the channel in the diffuser element and drip 363 into the lower reservoir (e.g., a second reservoir). As the oil drips into the lower reservoir, there may be some bubbles 366 that flow upward through the oil of the upper reservoir. After some time, all the oil in the upper reservoir will be collected (e.g., an oil 370) in the lower reservoir, and the oil drops will stop.

In an implementation, the time for an upper reservoir, full of oil, to empty by dripping into the lower reservoir is about 20 minutes. The exact time can vary, such as 6, 8, 10, 15, 25, 30, 40, 50, 60 (i.e., 1 hour), 90, or 120 minutes, and depend on factors such as channel size, temperature, and viscosity and amount of oil. Then the user can start the process over again by turning the diffuser over, such that the upper reservoir (e.g., second reservoir) becomes the lower reservoir (e.g., first reservoir), and the lower reservoir becomes the upper reservoir.

By use and evaporation over time, the fragrance oil will be consumed. When empty or partially empty, the user can refill or top off the fragrance oil with the same or different oil (e.g., different scent) by removing the diffuser element (which also acts as a stopper) from one of the reservoirs, and then refill that reservoir. The diffuser element is inserted back in the reservoir to complete the refill process. In some implementations, the package or kit with the fragrance diffuser is not prefilled with oil, and the user will fill the oil, such as described above.

The fragrant oil can be any liquid or oil with a volatile fragrance or aromatic constituent, such as an essential oil. The fragrant oil can be a mixture of a carrier oil and an essential oil. A carrier oil is an oil with a neutral smell and is generally less volatile than an essential oil. An essential oil is an oil that comes from a plant that has an aroma. Alternatively or in addition to the essential oil, the aromatic constituent may be a synthetic aromatic constituent (e.g., synthetic oil, aldehyde, ketone, or alcohol). The fragrant oil mixture can also include an alcohol (e.g., isopropyl alcohol or ethanol) and water. The alcohol can help emulsify the solution and also volatilize the aromatic constituent of the solution. The fragrant oil solution used may be, for example, one of many reed diffuser refill oils that are available to consumers.

Some examples of carrier oils include sweet almond, apricot kernel, avocado, evening primrose, jojoba, and others, and combinations of these. Some examples of essential oils include bergamot, clary sage, cinnamon bark, eucalyptus, gardenia, grapefruit, jasmine, lavender, lemon, lime, patchouli, peppermint, rosemary, spearmint, sweet orange, vanilla, tea tree, and thyme, and combinations of these. Some examples of synthetic fragrances include linen, apple, bananas, berries, citrus, cotton candy, caramel corn, kettle corn, apple pie, mandarin, meadow, rain, Christmas tree, pumpkin spice, chocolate, gingerbread, ocean breeze, floral bouquet, Hawaiian, and others, some of which may have arbitrary names or descriptions. A fragrance can be a combination of a plant-based or natural fragrance and a synthetic or artificial fragrance.

In an implementation, the diffuser element is made of wood, plant-based material, or other material with cellulose fibers. The cell walls of plant material are largely made of cellulose. The diffuser element absorbs the fragrant oil, and the surfaces of the diffuser element become wetted or saturated with the fragrant oil. These surfaces are exposed to the air of the exterior space. Through evaporation, the volatilized chemical compounds, which include molecules responsible for the fragrance, of the oil are carried into the air of the exterior space.

Some examples of woods that can be used for the diffuser element includes pine, oak, cherry, poplar, willow, rattan, cedar, fir, hemlock, redwood, spruce, beech, cypress, alder, aspen, birch, mahogany, rosewood, teak, wenge, maple, and others, and any combination of these. For example, for a two-part diffuser element (see below), one part may be made from one type of wood, while the other part is made from another type of wood.

The fragrance diffuser is a significant improvement over reed diffusers. Typically, current reed diffusers consist of one open container and several wooden reeds that stick through the opening. The reeds absorb the liquid on the bottom first, then have to be taken out of the container to be turned over so the saturated end can be exposed to open air and allowed to diffuse into the environment.

With the traditional reed diffuser, the air freshening process is messy because the liquid drips from the reeds and often causes damage to the surrounding furniture. And since the reeds need to be touched, the liquid also absorbs into the skin of the hands. There is no pleasant interactive element to the experience of refreshing the sent; scented reed saturates the air without the user's control and sometimes the scent is well beyond the user's comfortable level.

Unlike the reed diffuser where the reeds are turned over to expose the saturated reed ends to the air, the entire fragrance diffuser is flipped over to refresh the scent. When the fragrance diffuser is flipped over, the fragrance oil that had dripped to the bottom reservoir is flipped to become the top reservoir. And the fragrant oil once again wets or saturates the diffuser element.

Wood, plant-based, or cellulose fiber materials are used for the diffuser element due to their oil absorbing characteristic. These materials have interstices, intercellular spaces, or pores, or a combination, that trap the oil. Based on diffusion principles, the oil is conducted, via a capillary action, to surfaces where the oil can evaporate.

Specifically, the materials absorb oil into intercellular spaces or pores based on diffusion principles, which can be characterized based on Fick's laws of diffusion. Thus, for surfaces of the diffuser element where there is a hypertonic solution of the oil (e.g., oil has greater concentration than within the material), the oil is absorbed into the material until equilibrium is achieved. In equilibrium, the oil will be an isotonic solution in relation to the material. For surfaces of the diffuser element exposed to the air, there will be a hypotonic solution of the oil. The oil and fragrance will evaporate or diffuse into the air, and this will continue until equilibrium is achieved.

The diffuser element continues to dispense fragrance as long as this diffusion cycle continues—slowly moving oil from within the diffuser (where the oil is at a higher concentration) into the air of the room or space (where the oil is at a lower concentration). Equilibrium can be achieved under circumstances such as when the oil is no longer in contact with the diffuser element or when the oil has been entirely consumed.

To maintain the diffusion cycle of the fragrance, the inside surfaces oil should continue to be kept in contact with the oil. So, when the oil has completely drained into the lower reservoir, the user can flip over the diffuser to place the oil in contact with the diffuser element again (e.g., opposite diffuser element end). The flow of the oil in the diffuser is reversible, changing directions depending on which reservoir is the upper reservoir.

Except for the outer surfaces of the diffuser element, the system is completely sealed and enclosed. The oil is sealed in the unit, and unlike a reed diffuser, the oil cannot be easily spilled. There will be no drips that can occur when flipping the unit—unlike that may occur when flipping of reeds. The user's hand will not get oily because the user will flip the unit by holding and grabbing the reservoir surfaces, which are not oily.

The amount of oil that is absorbed by the diffuser element material depends on the amount of surface area touching the oil. The greater the surface area, the greater the absorption and rate at which oil can be conducted to the surfaces touching the air. In an implementation, a hole is formed (e.g., drilling using a drill bit) to allow oil to gradually or slowly drip from the upper reservoir to the lower reservoir.

This increases the surface area that is in contact with the oil, and also reduces the distance between the surfaces in contact with the oil and surfaces in contact with the air. In other implementation, the surface area in contact with the oil can be increased by drilling additional holes or openings into the diffuser element. Some of these holes may not necessarily go through the diffuser element entirely, from first reservoir to second reservoir. There may be other features used to increase the surface area, such as wings, slats, ridges, pins, spirals, grooves, recesses, trenches, protrusions, fins, or other patterns on the interior diffuser element surfaces.

Similar principles apply to the exterior diffuser element surfaces that are in contact with air. The greater the surface area, the greater the evaporation or diffusion of oil and fragrance into the air. In a specific implementation, there are a series of slats or ridges and grooves formed on the outer surface that increase surface area. In other implementations, there may be other features used to increase the surface area, such as wings, spirals, grooves, recesses, trenches, protrusions, fins, or other patterns.

Wood or plant-based materials usually have grains running through the material. These grains can be due to ribbons of cellulose running through the wood. These ribbons conduct water or nutrients in the plant. In an implementation, the diffuser element is made so that the grains extend in the same direction as the flow of the oil, which is a similar direction as water flow and diffusion (e.g., via osmosis through the plant cells) in the tree trunk or plant stem. By orienting the wood grain in the same direction as the water flow, this can generally increase a rate of diffusion and absorption of oil in the material. However, in other implementations, the diffuser element is made so that the grains extend in perpendicular to or in a different direction as the flow of the oil.

Figure 4:
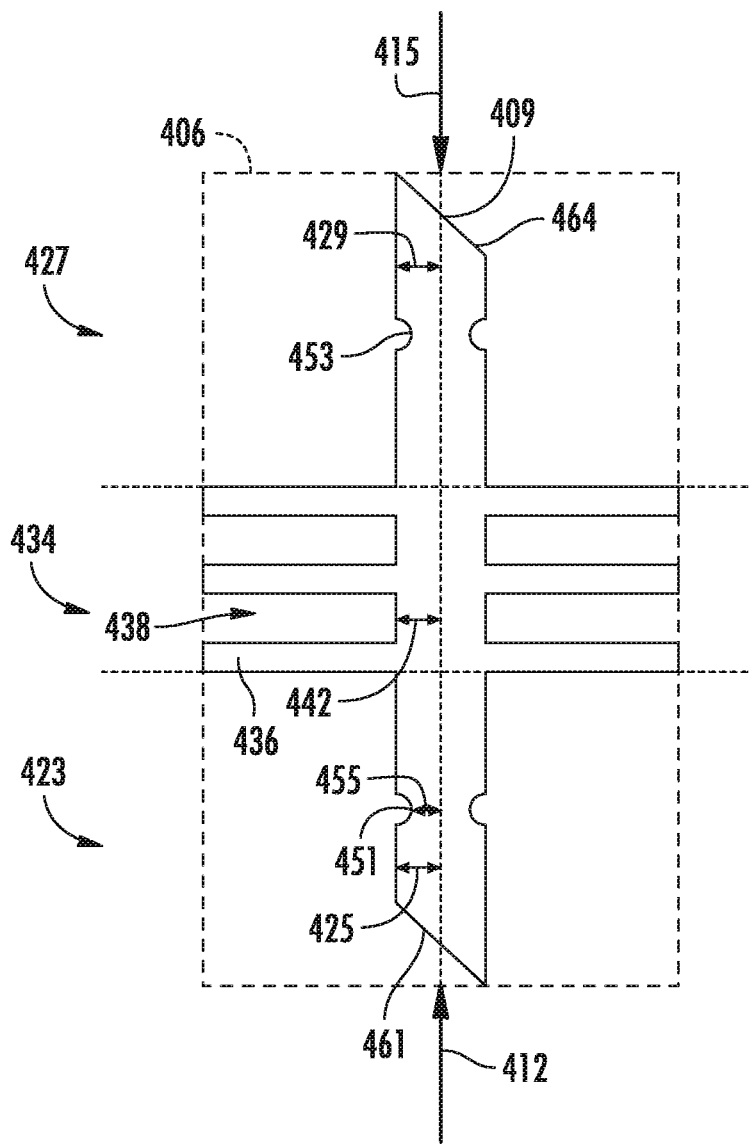
FIG. 4 shows a method of making a diffuser element from a block of material.
Figure 5:
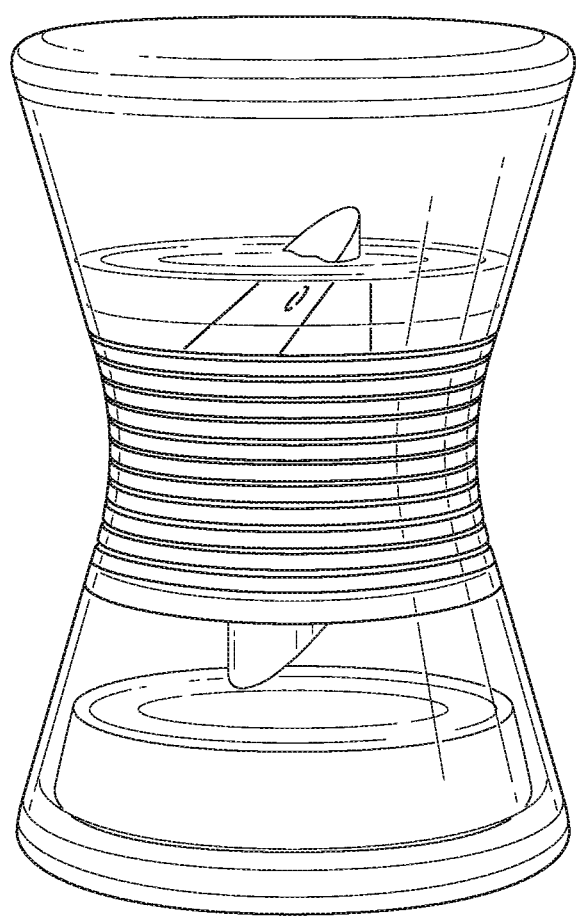
FIGS. 5-13 show another implementation of a fragrance diffuser.

FIG. 4 shows a method of making a diffuser element from a block of material. In an implementation, the diffuser element made from a block of wood, plant-based material, or other material with cellulose fibers. The block of wood can be a solid wood, plywood, pressed wood, fiberboard, particle board, medium-density fiberboard, hardboard, laminated wood, treated wood, wood fiber with a veneer, or others. The diffuser element can be manufactured using woodworking or machining techniques (e.g., wood turning or others) and equipment. Some examples of working equipment include lathe, saw, routers, cutters, and chisels, files, sander, sandpaper, grinder, belt sander, router, and others.

A technique to make the diffuser element is using wood turning and a lathe. FIG. 4 shows an example of a starting material block 406 (e.g., wood block) in broken lines. The block is mounted on the lathe along an axis 409 at two points 412 and 415. The block spins about the axis.

Woodworking tools (e.g., chisel, gouge, or other word carving tool) are used to create a first portion 423 with first radius 425 at a first end and a second portion 427 with a second radius 429. In an implementation, the first radius is the same as the second radius. Between the first and second portions is a third portion 434 that has the slats or ridges 436 that increase the surface area. Between the slats 436, a groove 438 is formed having a third radius 442. In an implementation, the third radius is the same as the first radius. The slats have a fourth radius (not shown) that is greater than the first radius. The first portion and second portions have a diameter that is narrower than a diameter of the slats in the third portion.

Additionally indentations 451 and 453 are formed in the first and second portions, respectively, which will be used to help retain the gasket, seal, or O-ring. The indentations or recesses will have a fourth radius 455 that is less than the first radius. The indentations form an indented or recessed ring about an axis of the diffuser element.

After the machined block is removed from the lathe, channel 322 can be formed by drilling using an appropriately sized drill bit. For example, an ⅛-inch drill bit can be used to drill a ⅛-inch channel. A ¼-inch drill bit can be used to drill a ¼-inch channel. A ⅜-inch drill bit can be used to drill a ⅜-inch channel. A 4-millimeter drill bit can be used to drill a 4-millimeter channel. The two ends 461 and 464 are formed by cutting the ends at an angle (e.g., 30, 45, 60, or 90 degrees) relative to the axis. The entire piece can be sanded to smooth the surface and remove any imperfections. The piece can further be stained or otherwise colored for appearance.

In other implementations, the diffuser element may be casted, molded, die cut, or formed using other techniques that result in a wood, plant-based material, or other material with cellulose fibers element with features described.

Figure 6:
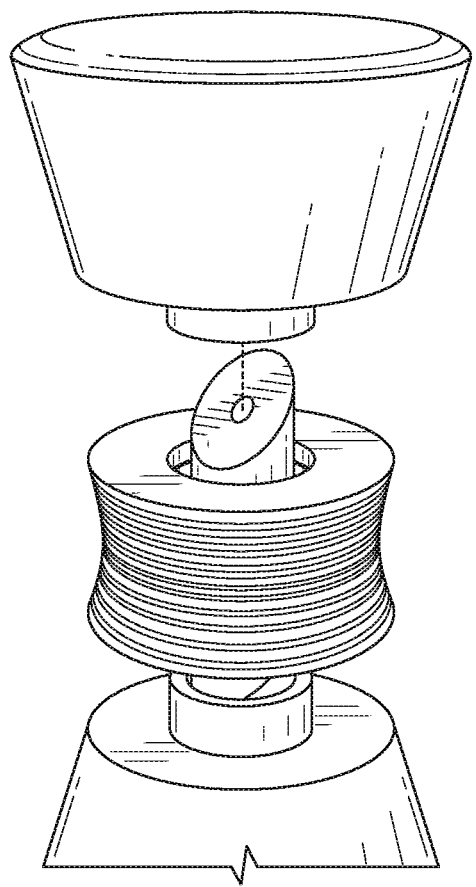

FIGS. 5-13 show another implementation of a scent glass or fragrance diffuser. This implementation may be referred as a "Sue" model. FIG. 6 shows an exploded view of the scent glass. The diffuser has a diffuser element, which can be referred to as a wooden "clockwork." The reservoirs are two hourglass halves, which can be two glasses or bottles that are the same.

Figure 7:
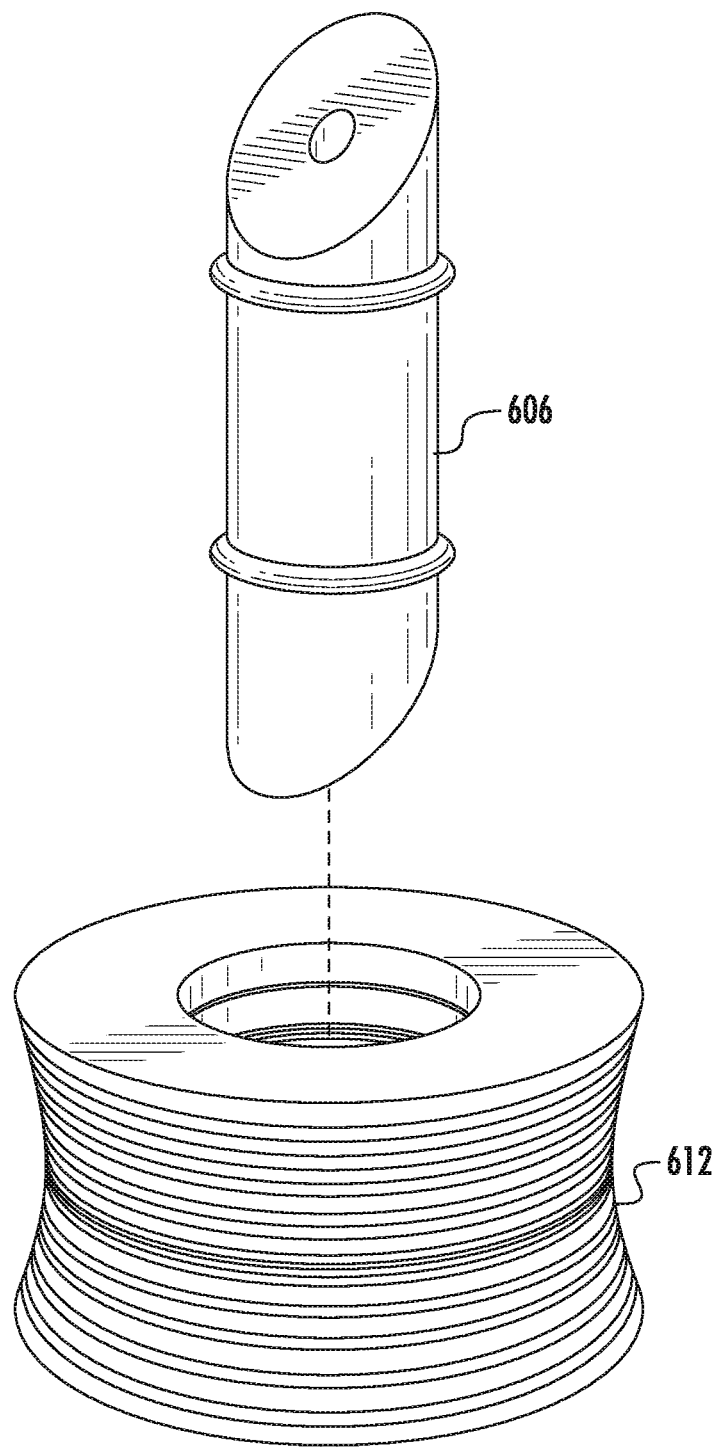

FIG. 7 shows an exploded view of a diffuser element. The diffuser element has two parts or portions, an inner portion 606 and outer portion 612. Inner portion 606 is cylindrical and includes a channel, gaskets, indentations (not shown), and angled ends. The inner portion can be a dowel that holds two O-rings that will seal a gap between the glass and the dowel. The two pieces of the diffuser element can be formed by woodworking techniques, such as described above.

This application describes some examples of implementations with specific dimensions, measurements, and values. These are not intended to be exhaustive or to limit the invention to the precise form described. The dimensions or measurements are in millimeters (or inches), radii of curvature in millimeters, angles in degrees. The values are approximate values. These values can vary due to, for example, measurement or manufacturing variations or tolerances or other factors. For example, depending on the tightness of the manufacturing tolerances, the values can vary plus or minus 5 percent, plus or minus 10 percent, plus or minus 15 percent, or plus or minus 20 percent.

Further, the measurements are for a specific implementation of the device, and other implementations can have different values, such as certain dimensions made larger for a larger-sized product, or smaller for a smaller-sized product. The apparatus may be made proportionally larger or smaller by adjusting relative measurements proportionally (e.g., maintaining the same or about the same ratio between different measurements). In various implementations, the values can be the same as the value given, about the same of the value given, at least or greater than the value given, or can be at most or less than the value given, or any combination of these.

Figure 10:
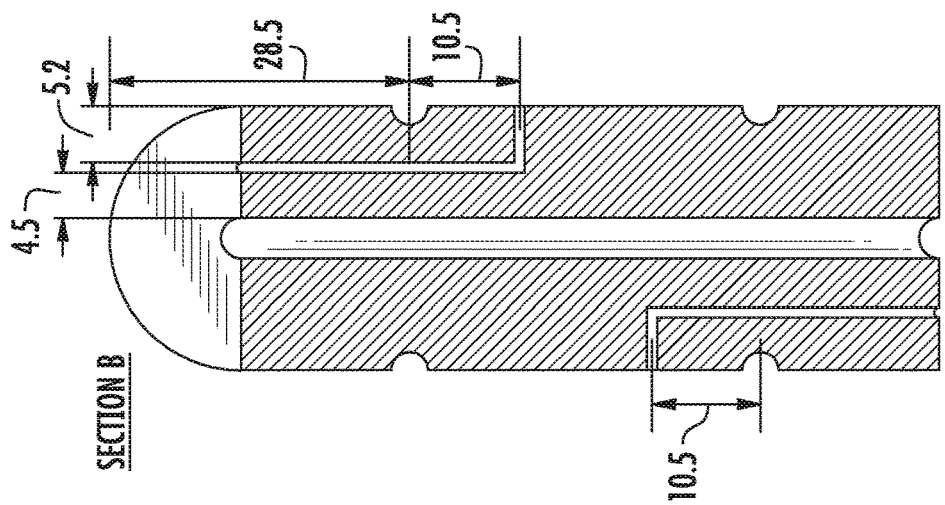
Figure 9:
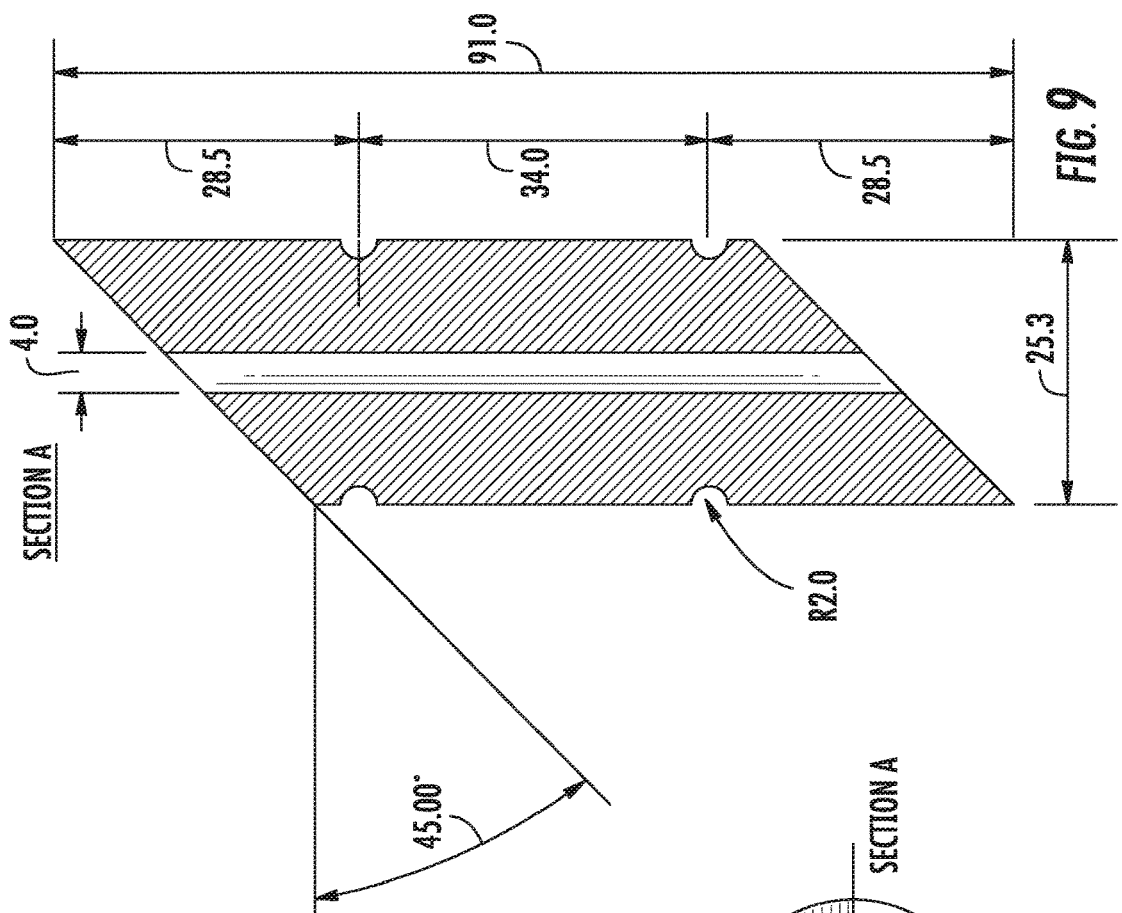
Figure 8:
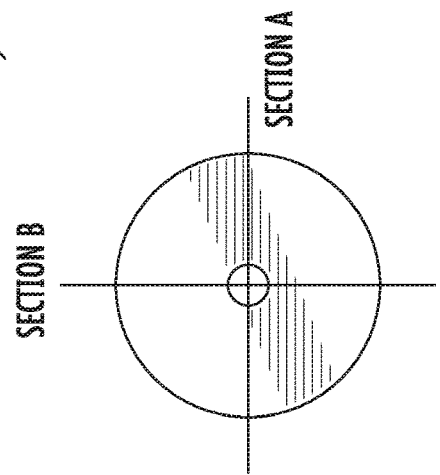

FIGS. 8-10 shows various views, details, and dimensions (in millimeters) of a specific implementation of the inner portion. In an implementation, the inner dowel is about 1 inch or about 25.3 millimeters in diameter. The dowel has a ⁵⁄₃₂-inch or 4-millimeter hole through its center. The ends are cut at about 45 degree angles. On both sides, there is a ¹⁄₂₃-inch or 1 millimeter L-shaped channel.

An outer portion 612 includes slats or ridges and grooves and a central core opening, into which the inner portion can be fitted into. The slats or ridges provide a relatively large surface area in order to release the scent. The inner portion and outer portions can be permanently attached together, or in other implementations, removably attached together. A permanent attachment may be by way of a friction fit, wood joint, staples, nails, screws, or glue, or a combination of these. Some examples of wood joining techniques include edge joint, miter joint, butt joint, dovetail joint, mortise and tenon joint, dowel joint, cross lap, tongue and groove, dado joint, and others.

The central core opening as two sections having a first radius or diameter and a section between the two that has a second radius or diameter. The first radius is greater than the second radius. The two sections are sized to permit the neck or stem of the glass to be inserted and hidden by the second portion of the diffuser element. The section with the second radius is sized to accommodate the first portion or dowel. When the first portion is inserted into the second portion, there will be gaskets on both sides or ends of the second portion. The first portion will be inserted into openings of the glasses, while the second portion hides the necks or stems of the glasses.

Figure 11:
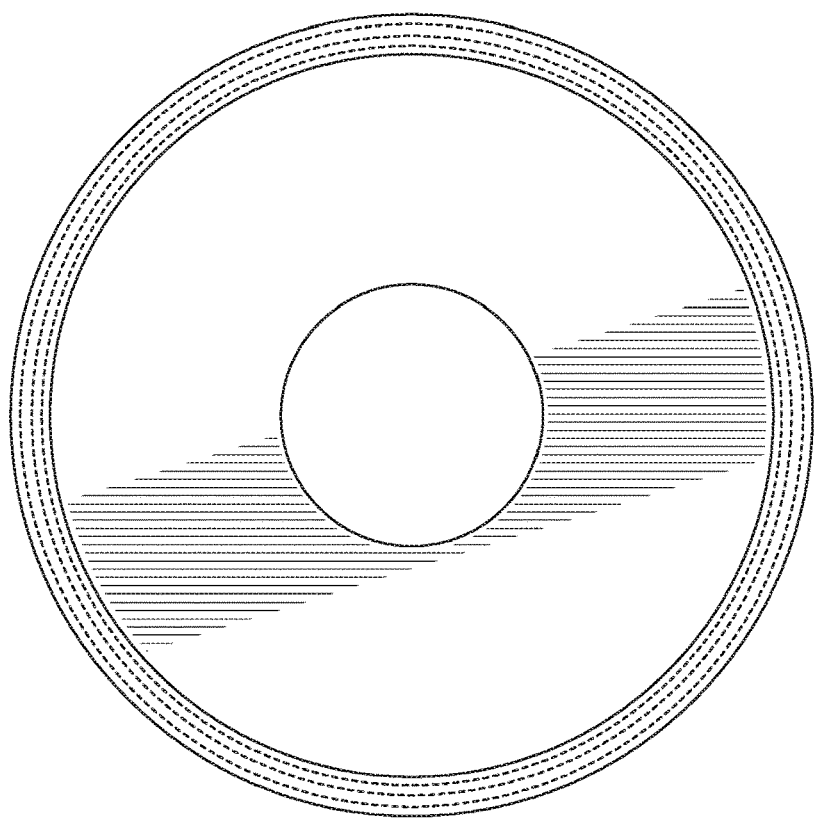
Figure 12:
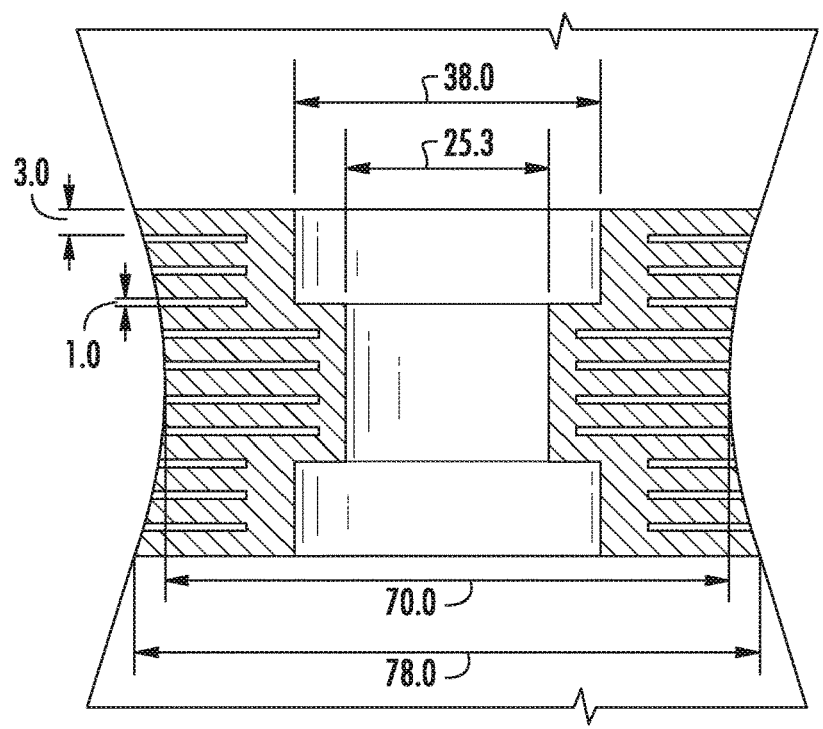

FIGS. 11-12 show various views, details, and dimensions of a specific implementation of the outer portion. The outer diffuser is cored out to fit the inner dowel and the glass opening neck or stem. The outside is sliced to provide a relative large surface area.

Figure 13:
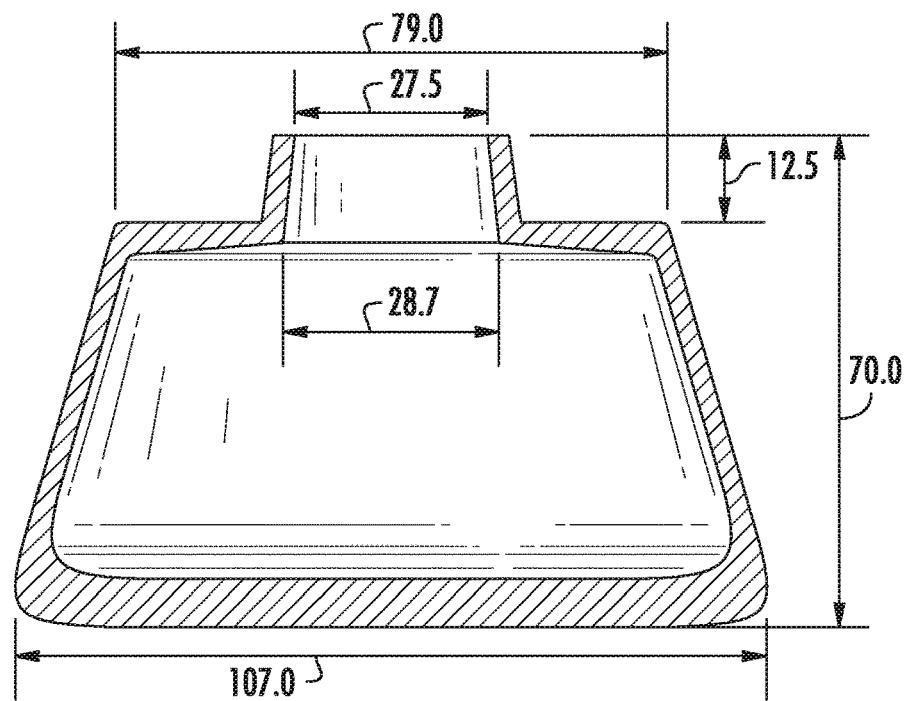

FIG. 13 shows details and dimensions of a specific implementation of the glass or bottle. The glass is conical and has a narrow neck. The thickness of the glass can vary. The bottle neck should be slightly conical (e.g., start at 28.7 millimeters and taper to 27.5 millimeters) to ensure a secure fit for the O-ring. The glass can be clear or translucent.

Figure 14:
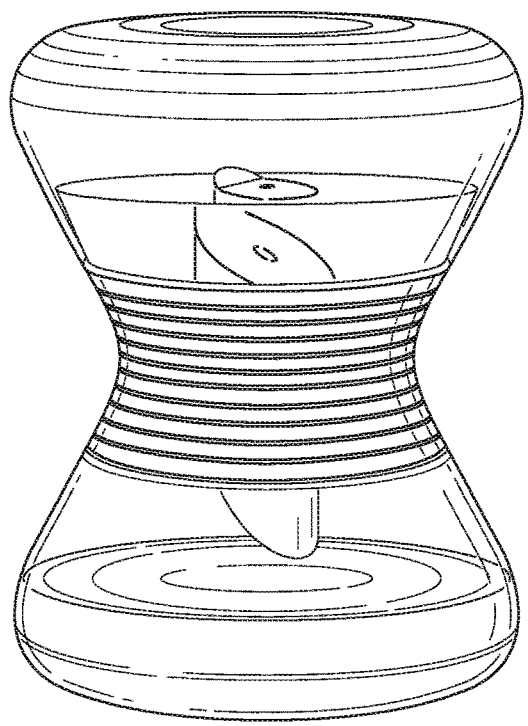
FIGS. 14-15 shows other implementations of fragrance diffusers.

FIG. 14 shows another implementation of a scent glass or fragrance diffuser, which may be referred to as a "Marc" model. An outer dimension of the Marc model can be 160 millimeters tall by 121 millimeters wide.

Figure 15:
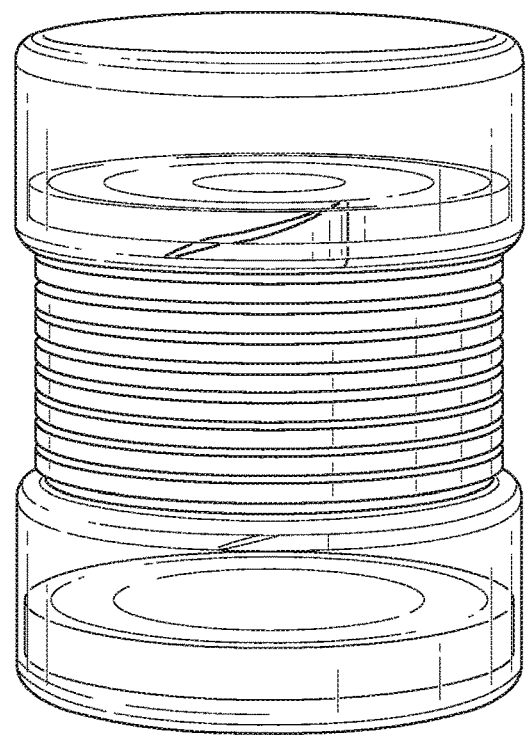
Figure 16:
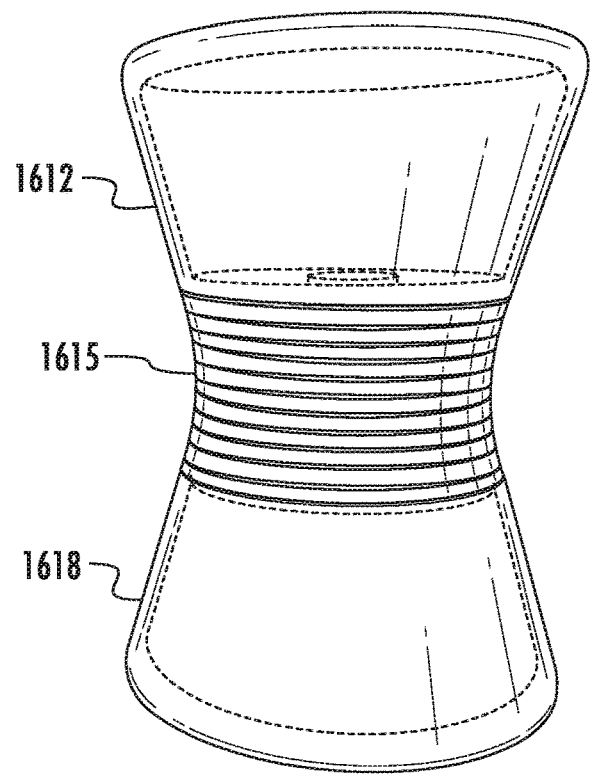
FIGS. 16-20 show another implementation of a fragrance diffuser.

FIG. 15 shows another implementation of a scent glass or fragrance diffuser, which may be referred to as a "Franz" model. An outer dimension of the Franz model can be 142 millimeters tall by 110 millimeters wide. In comparison to Marc and Franz, the Sue model can have an outer dimension of 160 millimeters tall by 106 millimeters wide.

FIGS. 16-20 show another implementation of a fragrance diffuser. This implementation is similar to other implementations described, having an upper bottle 1612 (referring to FIG. 16), wood ring or diffuser element 1615, and a lower bottle 1618. The wood ring has threaded female receptacles into which male threads of the bottles screw into.

Figure 17:
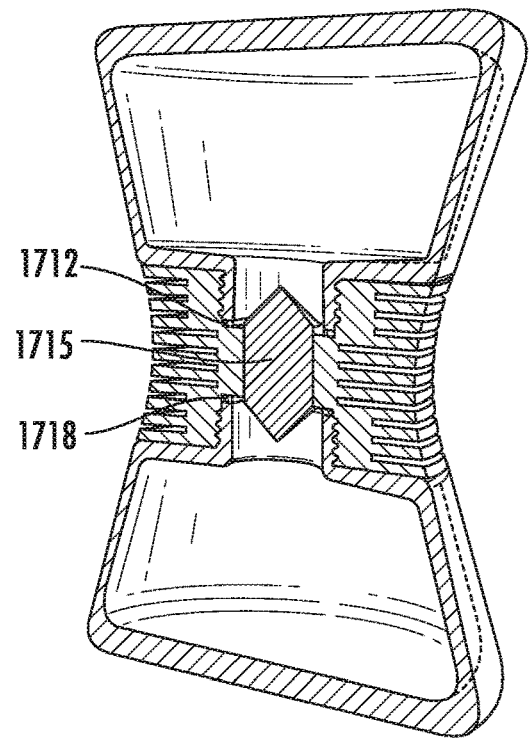
Figure 18:
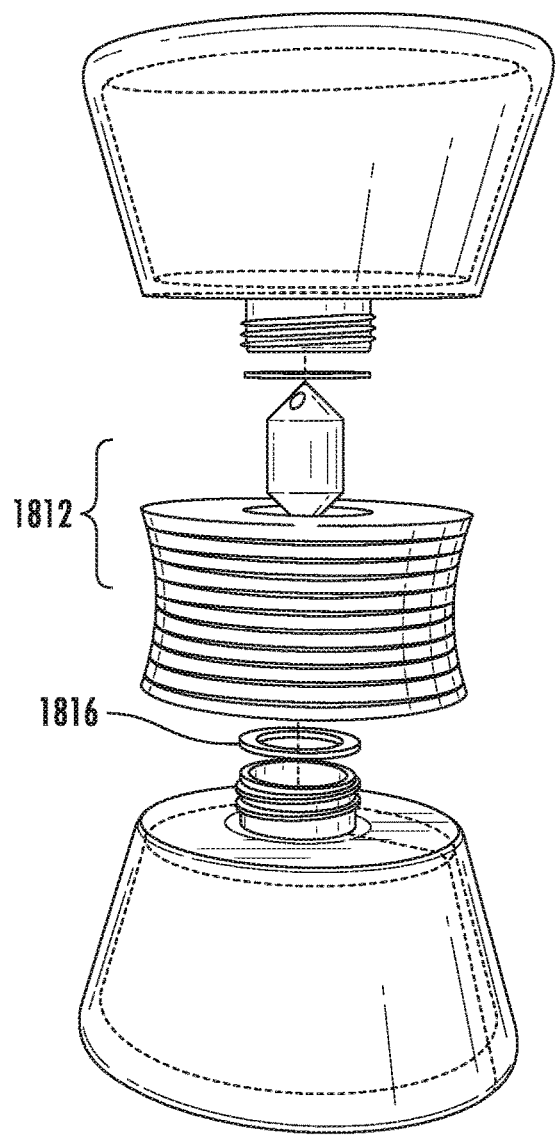
Figure 19:
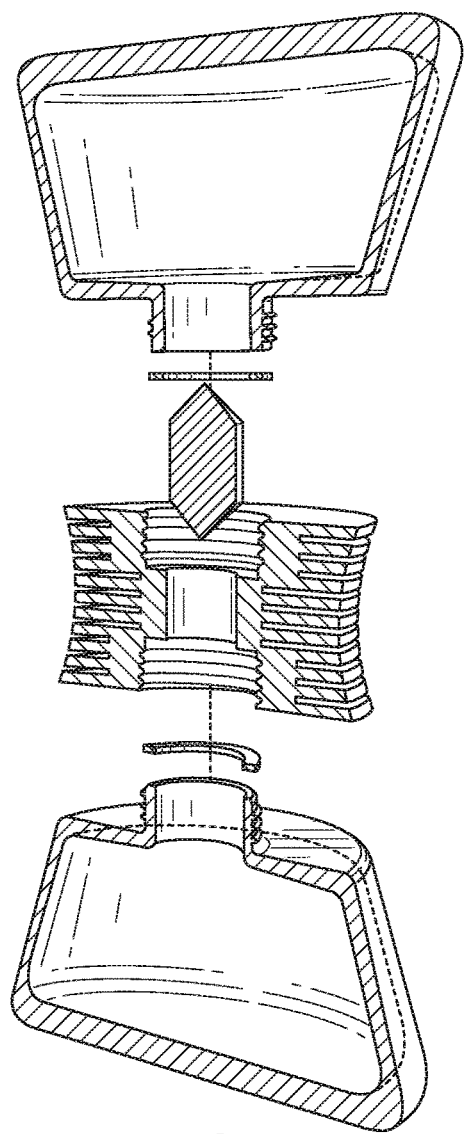
Figure 20:
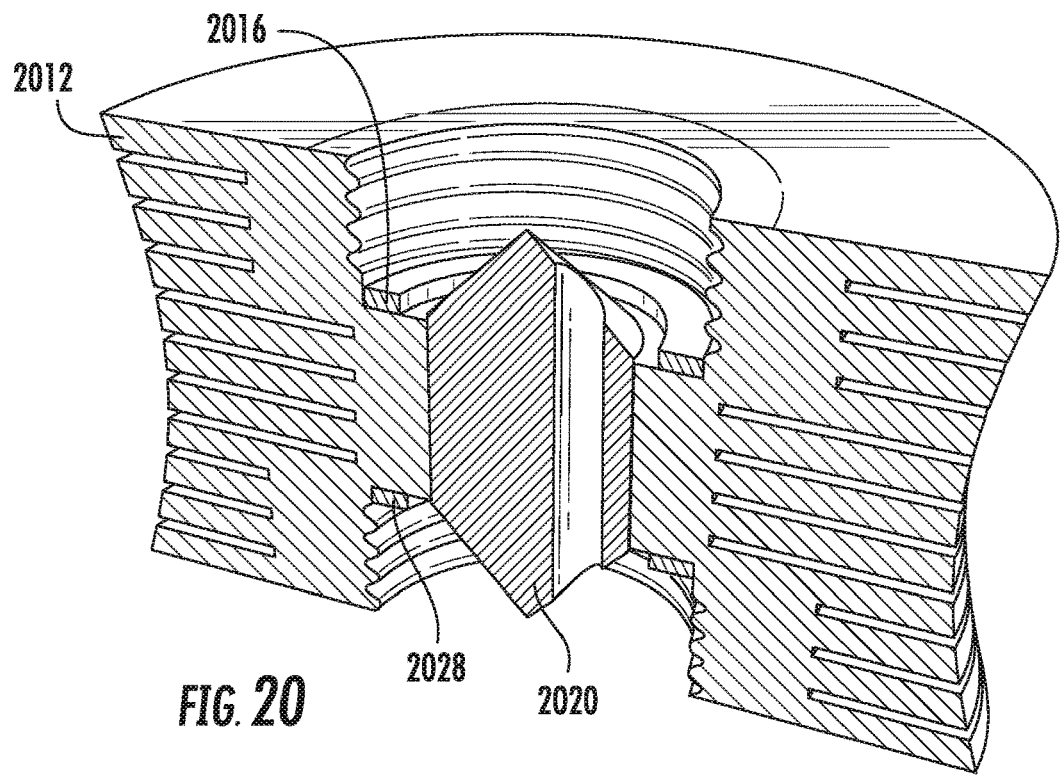

FIG. 17 shows a cross-sectional view of the fragrance diffuser. In a wood ring, there is a gasket 1712, a wood core 1715, and a gasket 1718. FIG. 18 shows an exploded view of the parts of the fragrance diffuser. There is a wood ring and wood core assembly 1812 and gasket 1816. FIG. 19 shows a cross-sectional exploded view of the parts of the fragrance diffuser. FIG. 20 shows details of a cross section of the diffuser element, which includes a wood ring 2012, gasket 2016, wood core 2020, and gasket 2028.

Referring to FIG. 17, gasket 1712 is a seal between a top of the upper bottle and the wood ring. Gasket 1718 is a seal between a top of the lower bottle and the wood ring. Scented oil in the upper bottle soaks into the wood core, which distributes the scented oil to the wood ring. The wood ring, with its slats, fins, or ridges distributes the scent into the air. The wood core also has a hole (now shown in FIG. 17), which allows scented oil to drop from the upper bottle to the lower bottle.

Gaskets 1712 and 1718 seal the tops of the bottles to the wood ring. The wood core and wood ring are bonded or interlocked, so that liquid does not leak out of the diffuser between them. This bonding or interlocking can be by an adhesive or glue, laminate, cork, gasket material (e.g., gasket that oils liquid to seep through but not leak), coating, dowel, staple, nail, screw, tight friction fit, wood joint (e.g., dovetail joint, finger joint, lap joint, miter joint, dado joint, rabbet joint, mortise and tenon, bridle joint, tongue and groove, and others), or other types of bonding. In another implementation, the wood ring and wood core are integrated as a single-piece element.

Figure 21:
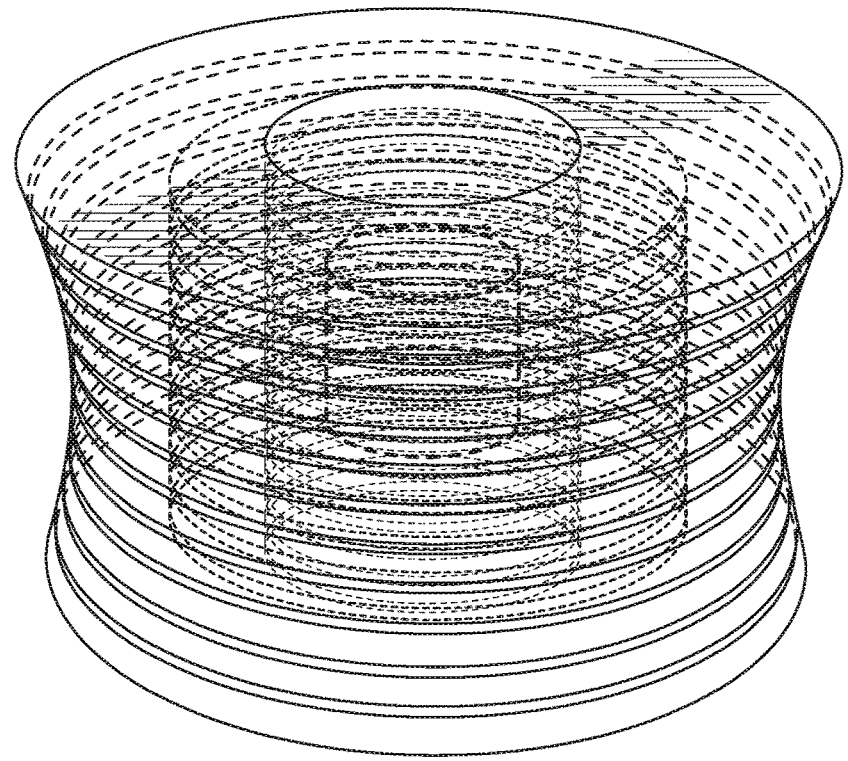

FIG. 21 shows a transparent perspective view of a wood ring. FIG. 22 shows a side view of the wood ring with a ghost view of an interior channel of the wood ring. The wood ring is symmetrical vertically about its center axis. The wood ring is symmetrical horizontally about a horizontal line or plane passing through a middle position of the wood ring.

The wood ring is threaded on top and bottom. There is a through hole (e.g., diameter of 18 millimeters) in its center. The top three slots or grooves are less deep (e.g., radius of 25 millimeters from center). The four middle slots are deeper (e.g., radius of 16 millimeters from center. A specific implementation has features with measurements or dimensions as listed in table A.

TABLE A

| Feature | Measurements (millimeters) |
| --- | --- |
| 2212 | 32 |
| 2215 | 29 |
| 2218 | 18 |
| 2221 | 16 |
| 2225 | 25 |
| 2228 | 78 |
| 2232 | 1 |
| 2235 | 3 |
| 2242 | 13 |
| 2245 | 16 |
| 2248 | 13 |
| 2252 | 42 |

For a top screw opening, feature 2212 is a width or diameter of the threaded receptacle to a bottom of the threads. Feature 2215 is a width or diameter of the threaded receptacle to a top of the threads. Feature 2218 is a width or diameter of a channel or opening between the upper and lower portions of the wood ring.

For a bottom screw opening, feature 2221 is a radius of the threaded receptacle to a bottom of the threads. This is a width between the center of the channel to a first wood end position between wood slats that extend from across a length 2245 of the center channel vertically. Feature 2225 is a width or radius of from the center of the channel to a second wood end between wood slats that extend from across a length 2248 of the bottom screw opening vertically. Feature 2228 is a width or diameter of a bottommost slat.

Feature 2242 is a length of a top screw opening vertically. Feature 2242 has symmetry with feature 2248, which is for the bottom screw opening. Feature 2252 is a horizontal length of the wood ring.

FIGS. 23A-23D show details of a wood core element of a fragrance diffuser. The wood core fits into the channel or through hole of the wood ring. FIG. 23A shows a first side view. FIG. 23B shows a second side view. FIG. 23C shows a perspective transparent view. FIG. 23D shows a top view.

The wood core is symmetrical vertically about its center axis. The wood ring is symmetrical horizontally about a horizontal line or plane passing through a middle position of the wood core. A specific implementation has features with measurements or dimensions as listed in table B.

TABLE B

| Feature | Measurements |
| --- | --- |
| 2312 | 36 mm |
| 2315 | 9 mm |
| 2317 | 18 mm |
| 2319 | 9 mm |
| 2322 | 90 degrees |
| 2332 | 4 mm |
| 2335 | 4 mm |
| 2338 | 18 mm |

Feature 2312 is a horizontal length of the wood core. Feature 2315 is length of a cone-shaped upper portion of the wood core. Feature 2317 is a cylindrical shaft portion, which is connected between the cone-shaped upper portion and a cone-shaped lower portion of the wood core. Feature 2319 is a length of the cone-shaped lower portion of the wood core, which is a mirror image of the cone-shaped upper portion.

FIG. 23A shows in broken lines a channel that passes entirely through the wood core, from an upper surface of the cone-shaped upper portion through the cylindrical shaft portion to a lower surface of the cone-shaped lower portion. FIG. 23B shows a 90 degree rotation of the wood core, relative to what is shown in FIG. 23A.

This channel in the wood core is positioned off center. This channel is used to conduct liquid from the upper reservoir to the lower reservoir. By being positioned off center (rather than, for example, in the center), the channel is shifted to the lower section of the chamfer. This way it is closer to the seal or a bottom edge of the cone and will allow more of the scent oil to drain from the upper vessel. If the channel was higher up (e.g., centered), some of the scent oil would pool and not be able to drain into the lower vessel.

Referring to FIG. 23D, feature 2332 is a distance between a center of the wood core to a center of the channel. Feature 2335 is a diameter of the channel. Feature 2338 is a diameter of the wood core.

Figure 24:
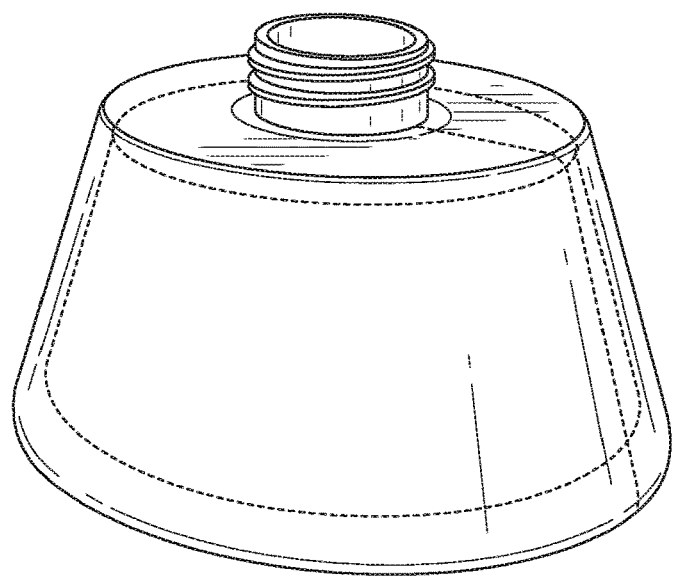
FIGS. 24-25 show details of a bottle of a fragrance diffuser.
Figure 25:
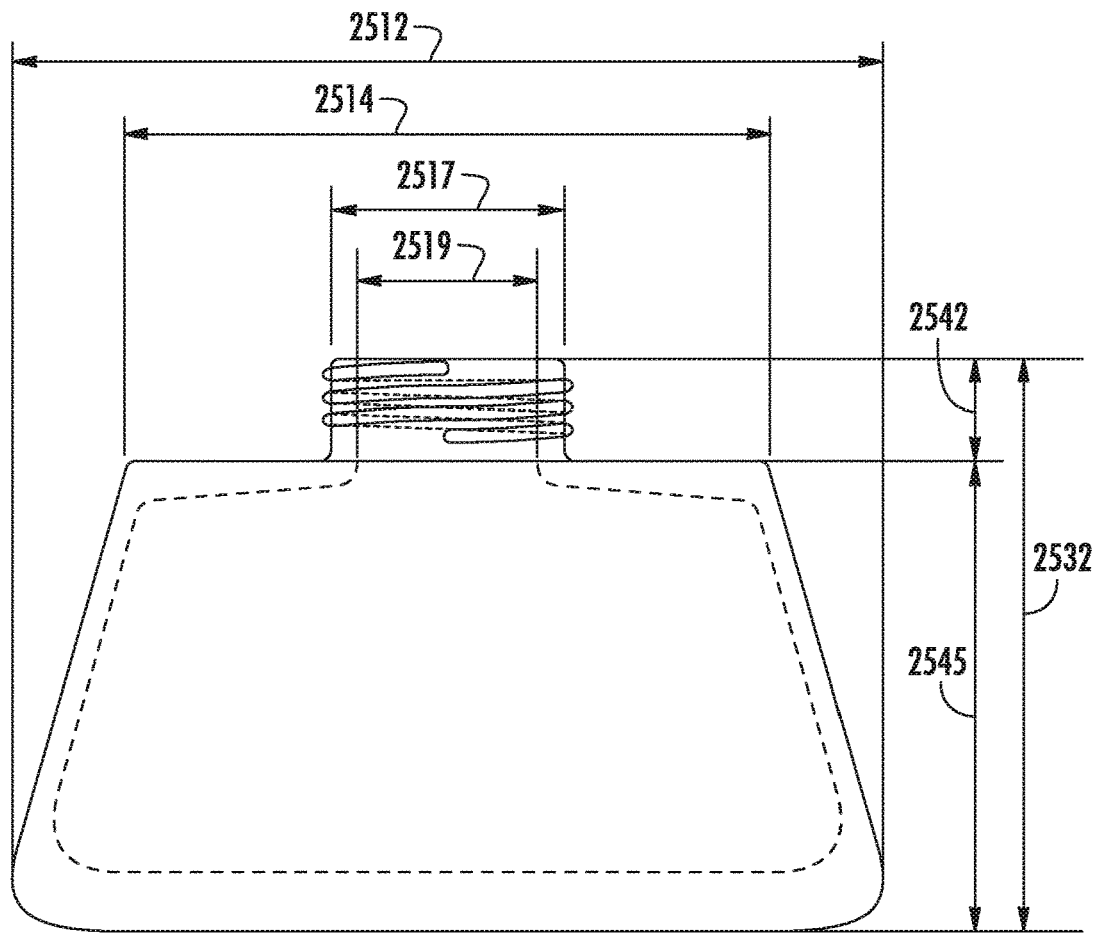

FIGS. 24-25 show details of a bottle of a fragrance diffuser. FIG. 24 shows a perspective transparent view of the bottle. FIG. 25 shows a side view of the bottle, including broken lines to show an outline of an interior space of the bottle. The fragrance diffuser has two bottles, which are the same in an implementation. A specific implementation has features with measurements or dimensions as listed in table C.

TABLE C

| Feature | Measurements (millimeters) |
| --- | --- |
| 2512 | 107 |
| 2514 | 79 |
| 2517 | 29 |
| 2519 | 22 |
| 2532 | 71 |
| 2542 | 13 |
| 2545 | 58 |

Feature 2512 is a maximum width or diameter of the bottle. The bottle is widest at its bottom. Feature 2514 is a width or diameter of the bottom at its upper rim. Feature 2517 is an outer diameter of the threaded portion of the bottle. Feature 2519 is an inner diameter of the threaded portion of the bottle. The threaded portion is connected to the upper rim of the bottle.

Feature 2532 is a total height of the bottle, including both the threaded portion and a jar portion. Feature 2542 is a height of the threaded portion. Feature 2545 is a height of the jar portion.

Figure 26:
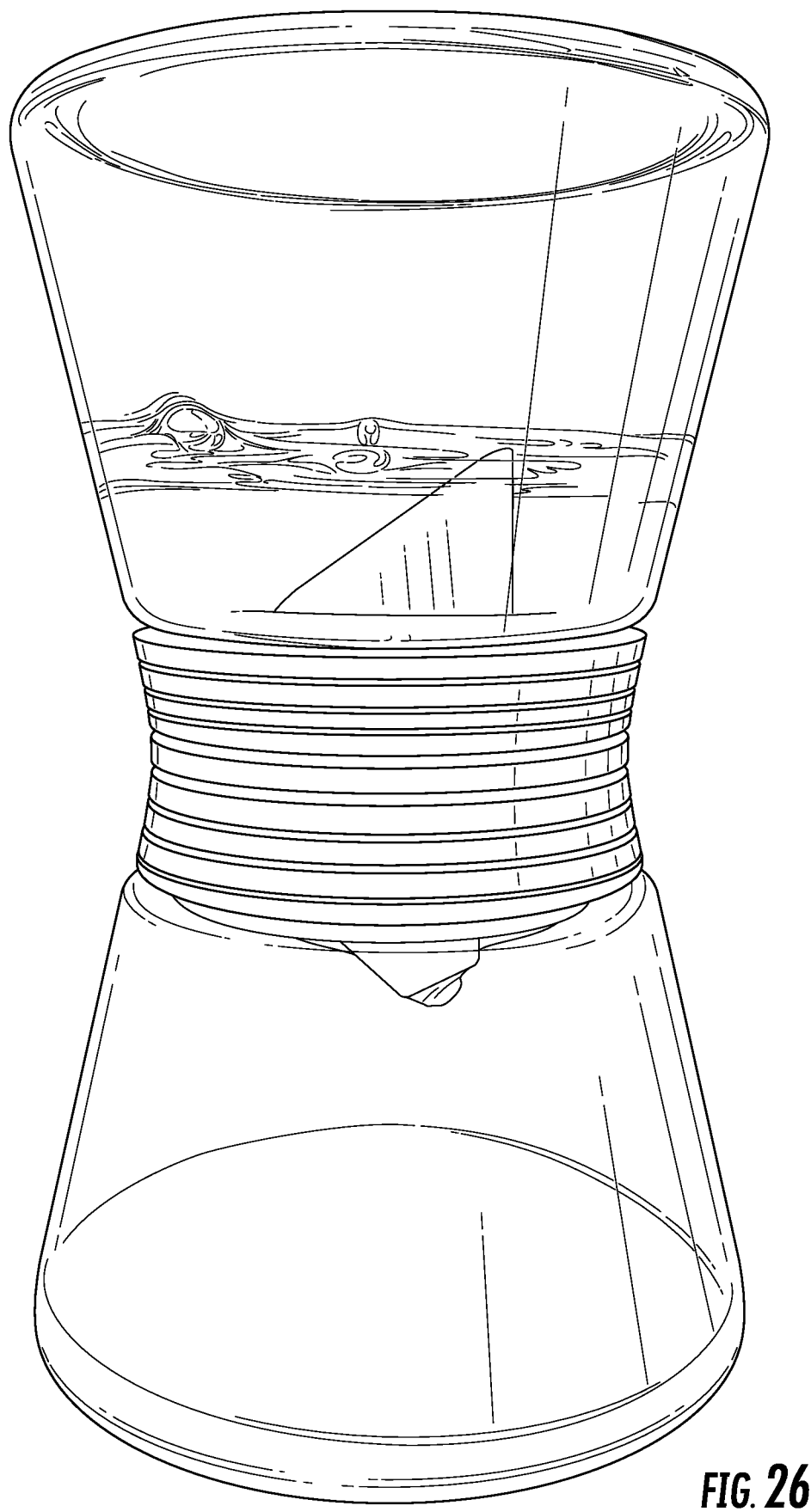
FIG. 26 shows an implementation of a fragrance diffuser.

FIG. 26 shows an implementation of a fragrance diffuser.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An apparatus comprising:
   a first reservoir comprising a first opening to a first chamber of the first reservoir;
   a second reservoir comprising a second opening to a second chamber of the second reservoir;
   a diffuser element, wherein the diffuser element is coupled between the first opening of the first reservoir and the second opening of the second reservoir, and an outer surface of the diffuser element comprises a plurality of slats and grooves, and
   the diffuser element comprises an inner portion and an outer portion, wherein the outer portion comprises the plurality of slats and grooves and a through hole, and the inner portion is adapted to fit into the through hole of the outer portion; and
   a first channel, extending through the diffuser element, the first channel coupling the first chamber to the second chamber, wherein the first channel is formed in the inner portion of the diffuser element.

2. The apparatus of claim 1 wherein the slats extend parallel to each other.

3. The apparatus of claim 1 wherein the diffuser element comprises cellulose.

4. The apparatus of claim 1 wherein the diffuser element comprises wood from at least one of pine, oak, cherry, poplar, willow, rattan, cedar, fir, hemlock, redwood, spruce, beech, cypress, alder, aspen, birch, mahogany, rosewood, teak, wenge, or maple tree.

5. The apparatus of claim 1 wherein the diffuser element comprises wood, and the inner and outer portions comprise the same wood material.

6. The apparatus of claim 1 wherein the plurality of slats extend in a direction that is transverse to the first channel.

7. The apparatus of claim 1 wherein an end of the inner portion comprises a sloped surface.

8. The apparatus of claim 1 wherein first and second ends of the inner portion comprise sloped surfaces.

9. An apparatus comprising:
   a first reservoir comprising a first opening to a first chamber of the first reservoir, wherein the first opening comprises a first male threaded portion;
   a second reservoir comprising a second opening to a second chamber of the second reservoir, wherein the second opening comprises a second male threaded portion;

a diffuser element, wherein the diffuser element is coupled between the first opening of the first reservoir and the second opening of the second reservoir, and an outer surface of the diffuser element comprises a plurality of slats and grooves;

a first threaded female receptacle, formed in a first end of the diffuser element, wherein the first threaded female receptacle couples with the first male threaded portion of the first reservoir;

a second threaded female receptacle, formed in a second end of the diffuser element, opposite to the first end, wherein the second threaded female receptacle couples with the second male threaded portion of the second reservoir;

a first gasket, coupled between the first threaded female receptacle of the diffuser element and the first opening of the first reservoir;

a second gasket, coupled between the second threaded female receptacle of the diffuser element and the second opening of the second reservoir;

a first channel, extending through the diffuser element, the first channel coupling the first chamber to the second chamber; and a second channel, positioned between the first and second threaded female receptacles of the diffuser element; and a diffuser inner portion, coupled in the second channel, wherein the first channel extends through the diffuser inner portion.

10. The apparatus of claim 9 wherein the plurality of slats extend in a direction that is transverse to the first channel.

11. The apparatus of claim 9 wherein the diffuser element comprises wood from at least one of pine, oak, cherry, poplar, willow, rattan, cedar, fir, hemlock, redwood, spruce, beech, cypress, alder, aspen, birch, mahogany, rosewood, teak, wenge, or maple tree.

12. The apparatus of claim 9 wherein a first axis through a center of the first channel is not collinear with a second axis through a center of the second channel.

13. The apparatus of claim 9 wherein the first reservoir comprises a bottom base portion having a larger diameter than an upper rim portion of the first reservoir.

14. The apparatus of claim 9 wherein first and second ends of the diffuser inner portion comprise sloped surfaces.

15. The apparatus of claim 9 wherein the diffuser element comprises cellulose.

16. An apparatus comprising:
a first glass reservoir comprising a first opening to a first chamber of the first reservoir;
a second glass reservoir comprising a second opening to a second chamber of the second reservoir;
a diffuser element, wherein the diffuser element is coupled between the first opening of the first reservoir and the second opening of the second reservoir, and
the diffuser element comprises an inner portion and an outer portion, wherein the outer portion comprises wood, a plurality of slats and grooves, and a through hole, and the inner portion is coupled to the through hole of the outer portion and comprises first and second ends comprising sloped surfaces; and
a first channel, extending through the diffuser element, the first channel coupling the first chamber to the second chamber, wherein the first channel is formed in the inner portion of the diffuser element and off of a center axis of the diffuser element.

17. The apparatus of claim 16 wherein the slats extend parallel to each other and transverse to the center axis of the diffuser element.

18. The apparatus of claim 9 wherein an end of the inner portion comprises a sloped surface.

19. The apparatus of claim 16 wherein the diffuser element comprises cellulose, or wood from at least one of a pine, oak, cherry, poplar, willow, rattan, cedar, fir, hemlock, redwood, spruce, beech, cypress, alder, aspen, birch, mahogany, rosewood, teak, wenge, or maple tree.

\* \* \* \* \*